United States Patent [19]

Suzuki et al.

[11] Patent Number: 4,613,500

[45] Date of Patent: Sep. 23, 1986

[54] POWDERY PHARMACEUTICAL COMPOSITION FOR NASAL ADMINISTRATION

[75] Inventors: Yoshiki Suzuki; Kunio Sekine; Tsuneji Nagai, all of Tokyo; Naoki Nambu, Kanagawa; Yuji Nishimoto, Tokyo, all of Japan

[73] Assignee: Teijin Limited, Osaka, Japan

[21] Appl. No.: 587,779

[22] Filed: Mar. 9, 1984

[30] Foreign Application Priority Data

Mar. 9, 1983 [JP] Japan ................. 58-37244

[51] Int. Cl.⁴ .............. A61K 9/14; A61K 37/26; A61K 37/30; A61K 39/145

[52] U.S. Cl. ........................ 429/85; 424/89; 424/92; 424/94; 424/46; 424/78; 424/80; 424/81; 424/38; 514/2; 514/3; 514/12; 514/13; 514/14; 514/15; 514/16; 514/17; 514/18; 514/19; 514/793; 514/781; 514/951

[58] Field of Search ............ 424/46, 85, 89, 92; 514/773, 774, 775, 776, 777, 778, 782, 951, 958, 213, 12-19

[56] References Cited

U.S. PATENT DOCUMENTS

| | | | |
|---|---|---|---|
| 2,445,300 | 7/1948 | Chambers | 424/89 |
| 2,445,301 | 7/1948 | Chambers | 424/89 |
| 2,798,835 | 7/1957 | Markham et al. | 424/89 |
| 2,908,614 | 10/1959 | Muggleton et al. | 424/89 |
| 2,946,724 | 7/1960 | Valentine | 424/89 |
| 2,959,325 | 11/1960 | Beard | 424/46 |
| 3,186,908 | 6/1965 | Rightsel et al. | 424/89 |
| 3,544,680 | 12/1970 | Plotkin | 424/89 |
| 3,594,471 | 7/1971 | Hertzberger et al. | 424/89 |
| 3,608,066 | 9/1971 | Illartein | 424/46 |
| 3,634,582 | 1/1972 | Hartley et al. | 424/15 |
| 3,755,557 | 8/1973 | Jacobs | 424/46 |
| 3,915,794 | 10/1975 | Zygraich et al. | 424/89 |
| 3,957,965 | 5/1976 | Hartley et al. | 424/15 |
| 4,053,583 | 10/1977 | Gits et al. | 424/89 |
| 4,110,427 | 8/1978 | Kalat | 424/46 |
| 4,136,168 | 1/1979 | Fontanges | 424/89 |
| 4,147,772 | 4/1979 | McAleer et al. | 424/89 |
| 4,225,581 | 9/1980 | Kreuter et al. | 424/89 |
| 4,235,876 | 11/1980 | Gits et al. | 424/89 |
| 4,251,509 | 2/1981 | Hanson et al. | 424/89 |
| 4,329,332 | 5/1982 | Couvreur et al. | 424/89 |
| 4,512,972 | 4/1985 | Schmidt-Ruppin | 424/89 |

FOREIGN PATENT DOCUMENTS

| | | |
|---|---|---|
| 0023359 | 2/1981 | European Pat. Off. . |
| 0094157 | 11/1983 | European Pat. Off. . |
| 2352556 | 12/1977 | France . |
| 668341 | 3/1949 | United Kingdom . |
| 716815 | 10/1954 | United Kingdom . |
| 1521000 | 8/1978 | United Kingdom . |
| 2029441A | 3/1980 | United Kingdom . |
| 1561835 | 3/1980 | United Kingdom . |
| 1571629 | 7/1980 | United Kingdom . |
| 1591405 | 6/1981 | United Kingdom . |

*Primary Examiner*—Shep K. Rose
*Attorney, Agent, or Firm*—Sughrue, Mion, Zinn, Macpeak & Seas

[57] ABSTRACT

What is provided by this invention is a powdery pharmaceutical composition for nasal administration comprising physiologically active polypeptide or its derivative such as calcitonin, insulin, etc. and a water-absorbing and water-insoluble base. The pharmaceutical composition allows polypeptide or its derivative to be efficiently absorbed through the nasal macous membrane when it is nasally administered.

18 Claims, 2 Drawing Figures

POWDERY PHARMACEUTICAL COMPOSITION FOR NASAL ADMINISTRATION

BACKGROUND OF THE INVENTION

1. Field of the Invention

This invention relates to a powdery pharmaceutical composition for nasal administration. More specifically, this invention relates to a powdery polypeptide or its derivative composition for nasal administration which comprises physiologically active polypeptide or its derivative such as calcitonin, insulin, etc. and a water-absorbing and water-insoluble base and allows said polypeptide or its derivative to be effectively absorbed through the nasal mucosa when nasally administered.

2. Description of the Prior Art

Because of the fact that peptide hormones such as insulin, calcitonin, etc. have a high molecular weight and that they are readily decomposed by proteolitic enzymes such as pepsin, trypsin, chymotrypsin, etc., the peptide hormones are not absorbed sufficiently enough to display a pharmacological effect efficaciously and accordingly they have been administered by parenteral injection.

However, since the administration by injection causes pain, various attempts to develop alternative methods of administration have been made. For example, there is a method of intrarectal administration of a suppository prepared by use of such salicylic acid derivatives as sodium salicylate, 3-methoxy sodium salicylate, and 5-methoxysalicylic acid as an absorption aid (J. Pharm. Pharmacol., 33, 334, (1981)). Besides this method, a method of intrabronchial administration (Diabetes, 20, 552, (1971)) and a method of eye-dropping administration (Diabetes Society's Epitomes, 237, (1974)) have been studied.

There are, however, drawbacks to all of these methods in that they require much larger doses than injection and that their absorption is varied and accordingly any of them have hardly been put to practical use as yet.

On the other hand, there is a method of nasal administration of an acidic aqueous solution of insulin, wherein such a surface active agent as sodium glycocholate is used as an absorption aid, known as the attempt to develop a method of intranasal administration (Diabetes, 27, 296, (1978)).

However, this method may not be regarded as an expedient means, since the preparation is prepared in the form of a liquid often causing the drug to flow out of the nasal cavity upon its administration into the nose and the use of a surface active agent in its preparation also causes inconvenience.

As the powdery pharmaceutical composition for nasal administration, U.S. Pat. No. 4,294,829 discloses a pharmaceutical preparation comprising lower alkyl ether of cellulose and a drug. This pharmaceutical composition is characterized in that its lower alkyl ether of cellulose absorbs moisture on the nasal mucous membrane, and takes the form of a viscous liquid to slowly flow over the nasal mucosa and releases the drug slowly. Since the composition of this type takes the form of a viscous liquid in the nasal cavity, the drug with a high molecular weight tends to stay within the lower alkyl ether of cellulose, becoming reluctant to the release from the composition. The composition of this type should, therefore, still undergo a significant improvement if it is to use such a drug with a high molecular weight as calcitonin, insulin, and the like.

SUMMARY OF THE INVENTION

One of the objects of this invention is to provide a powdery pharmaceutical composition for nasal administration.

Another object of this invention is to provide a powdery pharmaceutical composition for nasal administration aimed at application of physiologically active polypeptide or its derivative.

A further object of this invention is to provide a powdery pharmaceutical composition for nasal administration which allows physiologically active polypeptide or its derivative to be absorbed efficiently through the nasal mucosa without the use of an absorption aid.

Still another object of this invention is to provide a powdery pharmaceutical composition for nasal administration which especially allows polypeptides such as insulin, calcitonin, etc. to be absorbed efficiently through the nasal mucosa without the use of an absorption aid.

It is yet another object of this invention to provide a powdery pharmaceutical composition for nasal administration which allows physiologically active polypeptide or its derivative to be absorbed efficiently through the nasal mucosa and also has a sustained release effect.

It is still another object of this invention to provide a powdery pharmaceutical composition for nasal administration having such a proper particle diameter as to make it possible to be administered efficiently in the nasal cavity when intranasally sprayed.

Other objects and advantages of this invention will become apparent from the following description.

According to this invention, these objects and advantages are achieved by a powdery pharmaceutical composition for nasal administration which comprises physiologically active polypeptide or its derivative and a water-absorbing and water-insoluble base.

BRIEF DESCRIPTION OF THE DRAWING

As shown in FIG. 1 and FIG. 2, the powdery pharmaceutical composition for nasal administration is a composition which allows polypeptide such as insulin, etc. to be absorbed at a satisfactorily high effiency.

DESCRIPTION OF THE PREFERRED EMBODIMENTS

Figure 1:
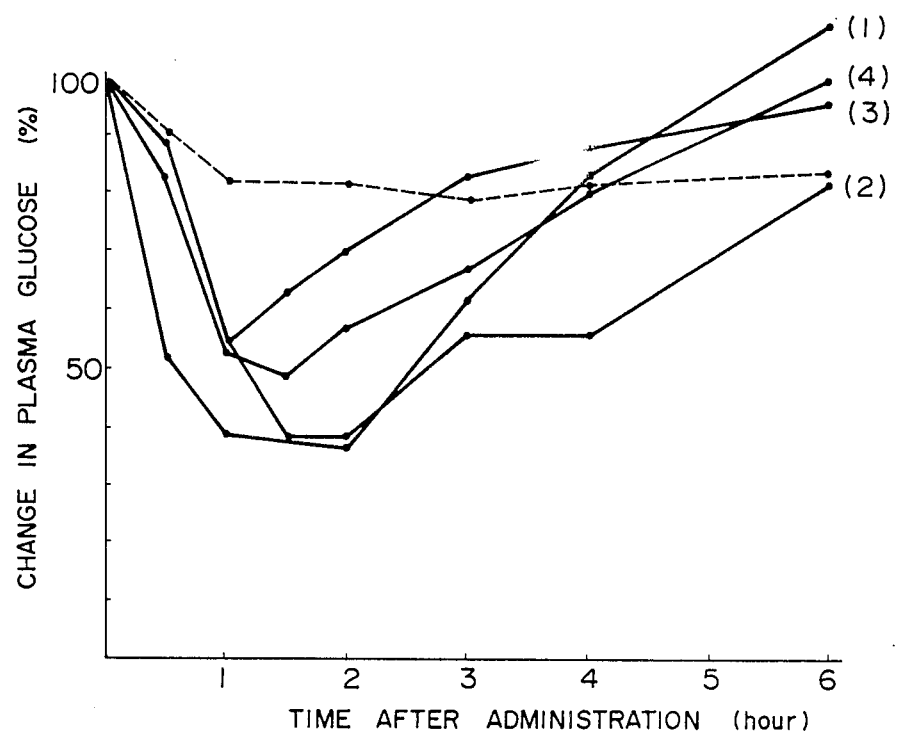
FIG. 1 shows the decrease (%) of the plasuma glucose levels after the nasal administration of a composition of this invention in which insulin is used as the polypeptide.

In this invention, the objective drug is physiologically active polypeptide or its derivative. As the polypeptide or its derivative, such polypeptide or its derivative with a molecular weight ranging from 1,000 to 300,000 are desirable in view of the fact that they are easily absorbed through the nasal mucous membrane. Especially those having a molecular weight ranging from 1,000 to 150,000 are more desirable.

Desirable physiologically active polypeptide or its derivative is exemplified in the following. For instance, such peptide hormones as insulin, angiotensin, vasopressin, desmopressin, felypressin, protirelin, luteinizing hormone releasing hormone, corticotropin, prolactin, somatropin, thyrotropin, luteinizing hormone, calcitonin, kallikrein, parathyrin, glucagon, oxytoxin, gastrin, secretin, serum gonadotrophin, growth hormone, erythropoietin, angiotensin, urogastrone and renin; such physiologically active proteins as interferon, interleukin, transferrin, histaglobulin, macrocortine and blood coagulation factor VIII; such enzyme proteins as lysozyme and urokinase; such vaccines as acellular and cellular pertussis vaccine, diphthelia vaccine, tetanus vaccine, influenza vaccine; and such toxoids as diphthelia toxoid, tetanus toxoid and toxoids of lymphocytosis promoting factor, and filamentors hemagglutinin (those are contained in acellular pertussis vaccine developed recently in Japan) may be mentioned. Of these polypeptide or its derivative mentioned above, peptide hormones, physiologically active protein and vaccine are desirable, and peptide hormones are especially more desirable, and among these peptide hormones, calcitonin, insulin, luteinizing hormone releasing hormone, desmopressin, vasopressin and oxytocin are particularly desirable and calcitonin and insulin are more particularly desirable. Among physiologically active protein, interferone is particularly desirable, and among vaccine, influenze vaccine and pertussis vaccine are particularly desirable.

For the preparation of powdery pharmaceutical compositions for nasal administration, the physiologically active polypeptide or its derivative is prefered to be those in the form of a powder. The physiologically active polypeptide or its derivative should desirably be water-soluble in view of the fact they are to be absorbed through the nasal mocous membrane. Here, "water-soluble" means that the polypeptide or its derivative is soluble on the human nasal mocous membrane or in a similar environment, or more concretely, it is soluble in an aqueous solution at pH around 7.4 at a temperature of about 36° C. to 37° C.

In case where polypeptides which are water-insoluble or hardly soluble in water are to be used, it is accordingly advisable, for instance, to adjust their pH, dissolve in water, and freeze-dry, thus making them water-soluble and in the form of powder.

Those polypeptides which are not in the form of powder should desirably be freeze-dried into powder before use.

The aforementioned polypeptide or its derivative can be used in combination with human serum albumin, mannitol, sorbitol, aminoacetic acid, amino acid, sodium chloride, phospholipid, etc. for the purpose of stabilization, or for the dual purpose of stabilizing and bulking.

In the preparation of powdery pharmaceutical compositions for nasal administration according to the present invention, a base having duplicity properties of water-absorbing and water-insoluble is used. By the terms of water-absorbing and water-insoluble, it is meant that the base has double properties of being water-absorbing and water-insoluble on the human nasal mucous membrane or in a similar environment, or more concretely, it is water-absorbing and water-insoluble at pH around 7.4 and at a temperature of 36° C. to 37° C. or thereabout.

Because of the use of a water-absorbing and water-insoluble base, the pharmaceutical composition of this invention are able to absorb the moisture on the nasal mucous membrane upon its administration into the nasal cavity, thus making each particle, which is not in the state of a viscous fluid and does not flow away immediately but diffuses moderately, stay at the site on the nasal mucosa where it adhered and allow the polypeptide or its derivative with a high molecular weight to come into thorough contact with the nasal mucosa, through which they are absorbed at a high efficiency. In this invention, the selection of such a base as mentioned above for use as the base of a polypeptide or its derivative preparation for nasal application has made it possible to make the polypeptide or its derivative to be absorbed effectively and let them display their pharmacological efficacy sufficiently without the use of an absorption aid.

The water-absorbing and water-insoluble bases which are to be used in this invention should be distinguished from those lower alkyl ethers of cellulose, or more particularly such lower alkyl ether of cellulose as hydroxypropyl cellulose which dissolves into a viscous fluid on the nasal mucous membrane. As the desirable examples of water-absorbing and water-insoluble base, the following ones may be mentioned.

They include, for instance, water-absorbing and water-insoluble celluloses such as crystalline cellulose, cellulose, α-cellulose, and cross-linked sodium carboxymethyl cellulose; water-absorbing and water-insoluble starches such as hydroxypropyl starch, carboxymethyl starch, cross-linked starch, amylose, amylopectin and pectin; water-absorbing and water-insoluble proteins such as gelatin, casein, sodium and casein; water-absorbing and water-insoluble gums such as gum arabic, tragacanth gum and glucomannan; and cross-linked vinyl polymers such as cross-linked polyvinyl pyrrolidone, cross-linked carboxyvinyl polymer or its salt, cross-linked polyvinyl alcohol and polyhydroxyethylmethacrylate. Of these mentioned above, water-absorbing and water-insoluble celluloses and cross-linked vinyl polymer are desirable, and water-absorbing and water-insoluble cellulose are more desirable and crystalline cellulose is especially desirable. Among cross-linked vinyl polymers, cross-linked polyvinylpyrolidone and cross-linked carboxy vinyl polymer or its salt are desirable.

Since the quantity of a water-absorbing and water-insoluble base to be used varies depending upon the polypeptide or its derivative to be used, it can not be defined indiscriminately; however, it is desirable in general to use it in appreciable amount of more than 10 times the weight of the polypeptide or its derivative especially more than 15 times, furthermore more than 20 times.

In preparing a pharmaceutical composition of this invention, said water-absorbing and water-insoluble base may be used in combination with a water-absorbing and water-soluble base. The combined use of a water-absorbing and water-soluble base adds some degree of solubility to a water-absorbing and water-insoluble base to produce the following effect. When the pharmaceutical composition is intranasally administered, the particles which comprise a water-absorbing and water-insoluble base and polypeptide or its derivative are dispersed over the nasal mucous membrane, and the water-absorbing and water-soluble base is dissolved into the state of a viscous fluid, which gives some degree of viscosity and flowage to the whole base of this invention, thus allowing the polypeptide or its derivative to be absorbed slowly which is known as a sustained release effect.

The water-absorbing and water-soluble base may be used by simply mixing it with the water-absorbing and water-insoluble base or by mixing it with the polypeptide or its derivative at the time of their freeze-drying. In case where the water-absorbing and water-soluble base is freeze-dried together with the polypeptide or its derivative, the mixture assumes the state in which particles of the polypeptide or its derivative are dispersed among particles of water-absorbing and water-soluble base and the final product of pharmaceutical composition comes to have much more sustained release effect.

As the water-absorbing and water-soluble base to be used in this invention, there are, for instance, polyacrylates such as sodium polyacrylate, potassium polyacrylate and amonium polyacrylate; lower alkyl ethers of cellulose such as methyl cellulose, hydroxyethyl cellulose, hydroxypropyl cellulose and sodium carboxymethyl cellulose; polyvinyl pyrrolidone, amylose, polyethyleneglycol and pullulan. Of these mentioned above, polyacrylate such as sodium polyacrylate; lower alkyl ether of cellulose such as methyl cellulose, hydroxypropyl cellulose, sodium carboxy-methyl cellulose; polyethyleneglycol and polyvinyl pyrrolidone are especially desirable. The quantity of a water-absorbing and water-soluble base to be used should desirably be 0.1 to 60 wt %, or more desirably 1 to 50 wt % against a water-absorbing and water-insoluble base.

In this invention, at least 90 wt % particles of the powdery composition desirably have an effective diameter of 10 to 250 microns. By controlling the particle diameter of the particles of the powdery composition in the abovementioned range, it becomes possible to have the powdery composition diffused widely over the nasal mucous membrane when intranasally administered, make the powdery composition stay long at the place where it has adhered, and facilitate the efficient intranasal administration upon pernasal spraying of the powdery composition through the nostril.

When the powdery composition, which contains more than 10 wt % particles having an effective diameter of less than 10 microns, is nasally administered by spraying, more particles will go further into the lungs or escape from the nostrils. Also, such powdery composition has difficulty in maintaining its effective drug concentration at a high level. On the other hand, when the powdery composition, which contains more than 10 wt % particles having an effective diameter of more than 250 microns, is intranasally administered, part of the particles on the nasal mucous membrane will readily separate from there, thus undesirably making its efficacy less stayable. It is especially desirable to control the powdery composition to have more than 90 wt % its particles measuring 20 to 150 microns in effective diameter.

The powdery composition of this invention may have any of the structures such as one in which the water-absorbing and water-insoluble base and polypeptide or its derivative form independent particles, one in which polypeptide or its derivative particles are adhered to the surface of the water-absorbing and water-insoluble base particle, one in which polypeptide or its derivative particles are dispersed in the water-absorbing and water-insoluble base particle, both forming separate phases of their own, or one in which polypeptide or its derivative particles are closely dispersed in the water-absorbing and water-insoluble base particle, thus forming a uniform dispersion.

The powdery composition of this invention, which has a structure in which the water-absorbing and water-insoluble base and polypeptide or its derivative form independent particle or polypeptide or its derivative particles are adhered to the surface of the water-absorbing and water-insoluble base particle, can be prepared by first adding polypeptide or its derivative to a water-absorbing and water-insoluble base, then mixing them by a mechanical process, and finally filtering them to obtain the desired composition with more than 90 wt % its particles preferably measuring 10 to 250 microns in effective diameter.

In case where a water-absorbing and water-soluble base is used in combination with a water-absorbing and water-insoluble base, both bases may be mixed together simultaneously with polypeptide or its derivatives in the mechanical mixing process.

The powdery composition of this invention, which has a structure in which polypeptide or its derivative particles are dispersed in the water-absorbing and water-insoluble base particle, both forming separate phases of their own, or polypeptide or its derivative particles are closely dispersed in the water-absorbing and water-insoluble base particle, thus forming a uniform dispersion, can be obtained by following the procedure mentioned below. It is prepared by firstly mixing polypeptide or its derivative with a water-absorbing and water-insoluble base by mechanical means, then compacting the obtained mixture under pressure, further pulverizing the compacted mixture, and finally filtering the resulting pulverulence to obtain the desired composition with more than 90 wt % its particles preferably measuring 10 to 250 microns in effective diameter. The powdery composition can also be obtained by thoroughly mixing polypeptide or its derivative with a water-absorbing and water-insoluble base in water to make a thin smooth pasty mixture, drying and pulverizing the mixture according to the ordinary methods, and finally passing the pulverized composition through a sieve.

In case where a water-absorbing and water-soluble base is to be used jointly, it may be admixed with polypeptide or its derivative and a water-absorbing and water-insoluble base in the mechanical mixing process, followed by the above-mentioned processes of compacting, etc., or a water-absorbing and water-soluble base may be introduced into the process wherein polypeptide or its derivative is mixed with a water-absorbing and water-insoluble base in the presence of water.

There is also another method of obtaining a powdery composition by joint use of a water-absorbing and water-soluble base, wherein a water-absorbing and water-soluble base is added to polypeptide or its derivative in the process in which polypeptide or its derivative is to be freeze-dried, thus both components being freeze-dried simultaneously as mentioned above.

In order to improve the properties, appearance or odor of the powdery pharmaceutical composition of this invention, it may, if desired, contain any of known additives such as coloring agents, preservatives, anticeptics corrigents, etc. As the coloring agents, there are, for instance, β-carotene, Red No.2, Blue No.1, etc.; as the preservatives, there are stearic acid, ascorbyl stearate, ascorbic acid, etc.; as the anticeptics, there are p-hydroxybenzoate, phenol, chlorobutanol, etc., and as the corrigents, there are menthol, citrus perfume, etc.

The powdery pharmaceutical composition of this invention can be directly used as a powder for a unit dosage form.

As the desirable form for administration, the powder can be filled in capsules such as hard gelatine capsules.

As the method of pernasally applying the powdery preparation to the nasal cavity by spraying, there is, for instance, a method in which a capsule filled with the powdery preparation is placed in a sprayer, which is exclusively designed for this purpose and equipped with a needle, then the capsule is pierced with the needle to have minute holes on both the top and bottom, and thereafter jets of powder are sent into the nasal cavity by means of ballooning, etc.

The following examples illustrate the present invention more specifically; however, it should be understood that these examples are given to explain the invention and not to limit the scope of the invention.

EXAMPLE 1

(i) Powdery pharmaceutical compositions for pernasal administration were obtained as follows:
 (a) 400 mg of water-soluble insulin powder, which was obtained by freeze-drying a solution prepared by dissolving insulin in 0.1N-HCl aqueous solution and further adding pure water thereto, and 3,600 mg of crystalline cellulose were placed in a mixer and mixed thoroughly to obtain a uniform powdery composition, at least 90 wt % particles of which had a particle diameter of 75 to 149 microns. Thus obtained powdery composition had the insulin activity of 2.55 units/mg.
 (b) 10 mg of insulin (25.5 units/mg) was dissolved in 0.2 ml of 0.1N hydrochloric acid. 200 ml of water was added thereto to give an aqueous solution of insulin and 40 mg of polyacrylic acid (Carbopol 934) was dissolved therein. About 30 ml of an aqueous solution of 0.01N sodium hydroxide was added to the solution to adjust it to pH 7.4. The solution was then freeze-dried to give a neutral and uniform powdery composition (I) with 5.1 units/mg of insulin, comprising insulin and sodium polyacrylate (neutral Carbopol 934).

Then, 50 mg of thus obtained powdery composition (I) and 50 mg of crystalline cellulose were put in a mortar and mixed thoroughly to obtain a uniform powdery composition (II), at least 90 wt % particles of which had a particle diameter of 75 to 149 microns. The obtained powdery composision (II) had the insulin activity of 2.55 units/mg.
 (d) The powdery compositions containing insulin prepared in the foregoing (a) and (b) were respectively filled in capsules to obtain insulin preparations for human pernasal administration.

(ii) The following comparative compositions were obtained to compare with the compositions of this invention.
 (d) 700 mg of water-soluble insulin powder (25.5 units/mg), which was obtained by once dissolving insulin, then followed by freeze-drying, and 6,300 mg of lactose were placed in a mixer and mixed well to give a uniform powdery composition, at least 90 wt % particles of which had a particle diameter of 75 to 149 microns.

Thus obtained powdery composition contained 2.55 units/mg of insulin.
 (e) 400 mg of water-soluble insulin powder (25.5 units/mg), which was obtained by once dissolving insulin and then freeze-drying the solution, and 3,600 mg of hydroxypropyl cellulose were placed in a mixer and mixed thoroughly to give a uniform powdery composition, at least 90 wt % particles of which had a particle diameter of 75 to 149 micron.

The powdery composition thus obtained contained 2.55 units/mg of insulin.

EXAMPLE 2

(Experiment of nasal administration of powdery insulin preparation in dogs.)

3 units/kg of the respective powdery compositions of insulin prepared in Example 1, (a), (b), (d), and (e) were administered intranasally to the male Beagle dogs (weighing 9.4 to 12.6 kg) which were anesthetized by intravenous injection of nembutal (containing 50 mg/ml of pentobarbital sodium) in 25 mg/kg doses. The administration of the powdery composition of insulin was carried out by spraying it into the nasal cavity with a double balloon through a polyethylene tube (about 2 mm in diameter) inserted about 3 cm into the nostril and the blood was withdrawn from the foreleg vein as time passed after the administration. The glucose level of plasma was measured by o-toluidine (Clinical Chemistry, 8, 215 (1962)). FIG. 1 shows the decrease (%) of the plasuma glucose levels from that before administration of insulin. The values shown in FIG. 1 are the average values of the four Beagle dogs. The change in plasma glucose levels after the nasal administration of 5 units/10 $\mu$l/kg, by use of a micropipette, of an aqueous suspension of original insulin powder is shown by a broken line in FIG. 1 for the sake of comparison. In FIG. 1, (1) indicates the case where crystalline cellulose was used as the base (Example 1, (a)), (2) the case where freeze-dried insulin-sodium polyacrylate and crystalline cellulose were used (Example 1, (b)), (3) the case where lactose was used as the base (Example 1, (d)), and (4) the case where hydroxypropyl cellulose was used as the base (Example 1, (e)) respectively.

It is clear from FIG. 1 that the compositions in which crystalline cellulose is used show a high efficient absorption of insulin and that the composition in which sodium polyacrylate is used in combination with crystalline cellulose show a high efficient absorption of insulin as well as a sustained release effect.

EXAMPLE 3

(i) 100 mg of porcin insulin was dissolved in 1 ml of 0.1N hydrochloric acid, to which 40 ml of dist. water was added to obtain an insulin solution. The obtained solution was freeze-dried to give water-soluble insulin powder (26.3 units/mg). The following powdery composition (a) of this invention was obtained from this insulin powder.
 (a) 20 mg of the water-soluble insulin powder obtained in the above (26.3 units/mg) and 140 mg of crystalline cellulose were weighed into a mortar and mixed thoroughly to obtain a uniform powdery composition. The powdery composition thus obtained contained about 3.3 units/mg of insulin.

(ii) With the purpose of comparing with the preceding powdery composition (a) of this invention, the following comparative powdery compositions (b) and (c) were prepared from the aforementioned insulin powder.
 (b) 15 mg of the water-soluble insulin powder (26.3 units/mg) and 105 mg of lactose were put in a mortar and mixed well to obtain a uniform powdery composition. The obtained powdery composition contained 3.3 units/mg of insulin.
 (c) 20 mg of the water-soluble insulin powder (26.3 units/mg) and 140 mg of hydroxypropyl cellulose were placed in a mortar and mixed thoroughly to obtain a uniform powdery composition. The powdery composition thus obtained contained about 3.3 units/mg of insulin.

EXAMPLE 4

(Experiment of nasal administration of powdery insulin preparation in rabbit.)

Figure 2:
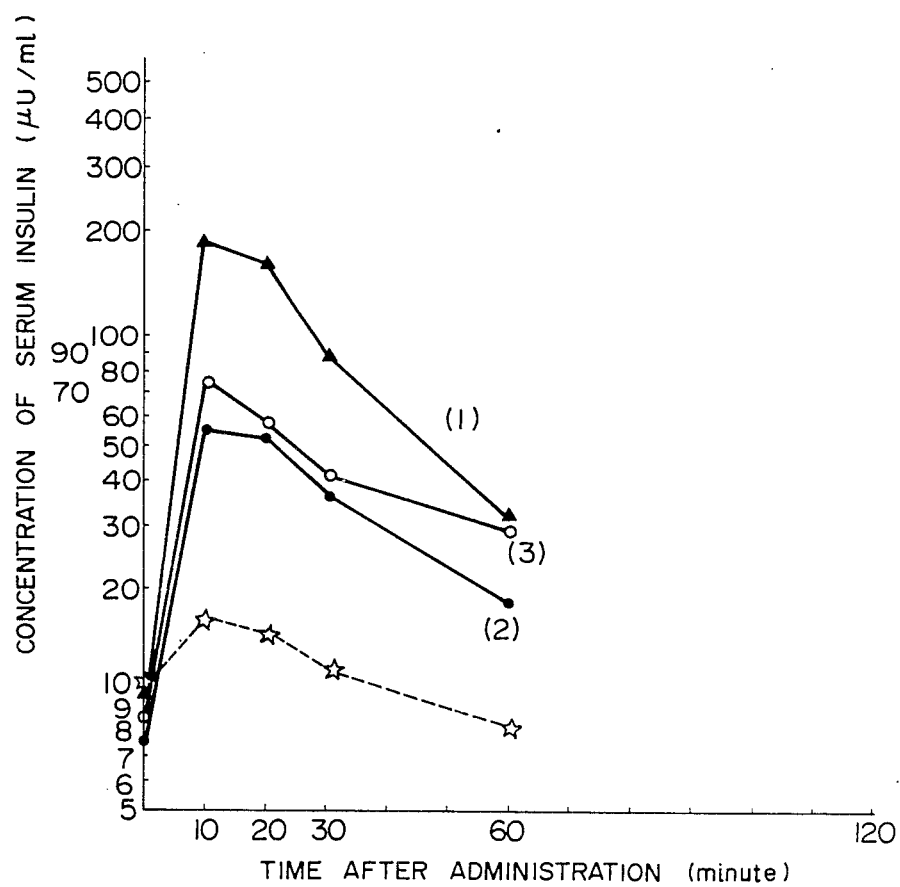
FIG. 2 shows the serum insulin livels after the nasal administration of a composition of this invention in which insulin is used.

10 units/head of the respective powdery composition of insulin prepared in Example 3, (a) to (c), were administered intranasally to which native male rabbits (weighing 3.0 to 3.5 kg). The blood was withdrawn from the ear vein 10 minutes, 20 minutes, minutes, and 60 minutes after the administration and also before the administration. The administration of the powdery composition of insulin was carried out by use of a sprayer specially modified for animal use while the rabbits were lightly anesthetized by ether or not. The insulin level of the serum was determined according to the radioimmunoassay. The result is shown in FIG. 2 in which the values are the average values of the three rabbits. Also, the result, which was obtained from the experiment conducted likewise with the nasal administration of 10 units/50 µl/head, by use of a micropipette, of an aqueous suspension of original insulin powder, is shown by a broken line in FIG. 2 for the sake of comparison.

In FIG. 2, (1) indicates the case where crystalline cellulose was used as the base (Example 3, (a)), (2) the case where lactose was used as the base (Example 3, (b)), and (3) the case where hydroxypropyl cellulose was used as the base (Example 3, (c)) respectively.

It is clear from Table 2 that the composition of this invention shows a high efficient absorption of insulin.

EXAMPLE 5

2,000 mg of crystalline cellulose and 0.5 mg of freeze-dried [$ASU^{1.7}$]-eel calcitonin (4,000 MRC units/mg) were placed in a mortar and mixed most thoroughly to obtain a uniform powdery composition. The obtained powdery composition contained about 1 MRC unit/mg of [$ASU^{1.7}$]-eel calcitonin. The powdery composition was filled in the prescribed capsules with the capsule filler, each capsule containing 10 to 50 mg, to obtain a preparation for human nasal application.

Also, examples of preparation of calcitonin powdery compositions for animal experiment use are given in the following (a) and (b).

(a) 200 mg of crystalline cellulose and 0.3 mg of freeze-dried [$ASU^{1.7}$]-eel calcitonin (4,000 MRC units/mg) were put in a mortar and mixed thoroughly to obtain a uniform powdery composition. The obtained powdery composition contained 5.99 MRC units/mg of [$ASU^{1.7}$]-eel calcitonin.

(b) 100 mg of crystalline cellulose and 0.3 mg of freeze-dried salmon calcitonin (2,000 MRC units/mg) were placed in a mortar and mixed well to obtain a uniform powdery composition. The obtained powdery composition contained 5.98 MRC units/mg of salmon calcitonin.

EXAMPLE 6

(Experiment of nasal administration of powder calcitonin preparations in rabbits.)

6 MRC units/kg of the respective powdery compositions of calcitonin prepared in Example 5, (a) and (b), were administered intranasally to the white native male rabbits (weighing 2.5 to 3.0 kg). The blood was withdrawn from their ear veins before the administration and 1 hour, 2 hours, 4 hours, and 6 hours after the administration. The administration of the powdery composition was carried out in the same way as the second animal experiment made in Example 4. The concentration of the serum calcium before and after the administration was measured to study the absorbability of calcitonin through the nasal mucous membrane. The measurement of serum calcium levels was made with the use of the calcium measurement kit (IATRON Co.). The result is shown in Table 1 in which the decrease of serum calcium levels as compared with the serum calcium levels obtained before the administration of powdery preparation of calcitonin is shown in percentages. The levels described in the table are the average values of the three rabbits.

As control, 60 MRC units/50 µ/kg almost neutral aqueous solution of [$ASU^{1.7}$]-eel calcitonin was nasally administered and the result is shown in Table 1.

TABLE 1

| | Powdery preparation | | Decrease of serum calcium as compared with preadministration (%) | | | |
|---|---|---|---|---|---|---|
| | Base | Calcitonin dosage | 1 hour | 2 hrs | 3 hrs | 4 hrs |
| Preparation of this invention | Crystalline cellulose | [$ASU^{1.7}$]-eel calcitonin 6 MRC units/kg | 10.3 | 9.1 | 2.2 | 0.3 |
| | Crystalline cellulose | Salmon calcitonin 6 MRC units/kg | 9.6 | 7.5 | 0.7 | −0.3 |
| Control | Water | [$ASU^{1.7}$]-eel calcitonin 6 MRC units/kg | 2.7 | 1.7 | 0.0 | 0.7 |

EXAMPLE 7

490 mg of crystalline cellulose and 10 mg of freeze-dried vasopressin (70 to 100 units/mg) were put in a mortar and mixed throughly to give a uniform powdery composition. The obtained powdery composition contained 1.4 to 2.0 units/mg of vasopressin.

The powdery composition thus obtained was then encapsulated according to the prescription to give a preparation for human nasal application.

EXAMPLE 8

990 mg of crystalline cellulose was weighed into a mortar and 10 mg of freeze-dried luteinizing hormone releasing hormone was added thereto. They were mixed thoroughly to obtain a uniform powdery composition. The obtained powdery composition contained 10 µg/mg of luteinizing hormone releasing hormone and the powdery composition was then filled in the prescribed capsules to give a preparation for human nasal application.

EXAMPLE 9

950 mg of crystalline cellulose was placed in a mortar, to which 50 mg of interferon ($10^5$ units/mg), which had been freeze-dried together with human serum albumin, was added. They were mixed thoroughly to obtain a uniform powdery composition. The powdery composition thus obtained contained 5,000 units/mg of interferon and was encapsulated according to the prescription to obtain a preparation for human nasal application.

EXAMPLE 10

2,000 mg of crystalline cellulose and 1 mg of freeze-dried desmopressin acetate were mixed thoroughly in a mortar to obtain a uniform powdery composition. The obtained powdery composition contained 0.5 μg/mg of desmopressin acetate. This composition was encapsulated according to the prescription to give a preparation for human nasal application.

EXAMPLE 11

2,000 mg of crystalline cellulose and 0.5 mg (4,000 MRC units/mg) of freeze-dried [ASU$^{1.7}$]-eel calcitonin or 1.0 mg (2,000 MRC units/mg) of salmon calcitonin were placed in a mortar and mixed well to obtain a uniform powdery composition. The obtained powdery composition contained about 1 MRC unit/mg of [ASU$^{1.7}$]-eel calcitonin or salmon calcitonin.

10 to 50 mg of the powdery composition these obtained was then encapsulated according to the prescription to give a preparation for human nasal application.

EXAMPLE 12

199 mg of hydroxypropylcellulose and 1 mg (2,000 MRC units/mg) were dissolved in 50 ml of water. The solution was freeze-dried to give a uniform powdery composition with the salmon activity of 10 MRC units/mg, comprising salmon and hydroxypropylcellulose.

100 mg of the powdery composition and 900 mg of crystalline cellulose were placed in a mortar and mixed thoroughly to obtain a uniform powdery composition, at least 90 wt % particles of which had a particle diameter of 10 to 250 microns.

Thus obtained powdery composition contained 1 MRC unit/mg of the salmon calcitonin. 10 to 50 mg of the powdery composition these obtained was then encapsulated according to the prescription to give a preparation for human nasal application.

EXAMPLE 13

499 mg of hydroxypropylcellulose and 1 mg (4,000 MRC untis/mg) of [ASU$^{1.7}$]-eel calcitonin.

200 mg of the powdery composition and 800 mg of crystalline cellulose were placed in a mortar and mixed throughly to obtain a powdery composition, at least 90 wt % particles of which had a particle diameter of 10 to 250 microns.

EXAMPLE 14

One mg of formalin-detoxificated Partussis toxin (PT and 1 mg of formalin-treated filamentous hemagglutinin (F-HA), those were components of a cellular pertussis vaccine developed recently in Japan and 1,000 mg of crystalline cellulose were placed in a mortar and mixed well to obtain a uniform powdery composition.

The obtained powdery composition contained about totally 2 μg/mg of both components.

10 to 25 mg of this composition was then encapsulated according to the prescription to give a preparation for human nasal application.

Thus obtained powdery composition contained 1.6 MRC units/mg of [ASU$^{1.7}$]-eel calcitonin. 10 to 50 mg of the powdery composition these obtained was then encapsulated according to the prescription to give a preparation for human nasal application.

EXAMPLE 15

800 mg of hydroxypropylcellulose and 200 mg of powdery freeze-dried influenza HA vaccine were placed in a mortar and mixed well to obtain a uniform powdery composition. The powdery composition contained about 200 μg/mg of freeze-dried influenza HA vaccine. 50 mg of the powdery composition and 95 mg of crystalline cellulose were placed in a mortar and mixed well to give a uniform powdery composition, at least 90 wt % particles of which had a particle diameter of 10 to 150 microns. Thus obtained powdery composition contained 10 μg/mg of freeze-dried influenza HA vaccine. 10 to 30 mg of powdery composition these obtained was then encapsulated according to the prescription to give a preparation for human nasal application.

What we claim is:

1. A method for nasal pharmaceutical administration which comprises the step of contacting the nasal mucosa with an intranasally effective amount of a powdery pharmaceutical composition for nasal adminstration consisting essentially of: (A) a physiologically active polypeptide or its derivative selected from the group consisting of a peptide hormone, a physiologically active protein, an enzyme protein and a vaccine, and (B) a water-absorbing and water-insoluble base, wherein at least 90 wt % of the particles of said composition have an effective diameter ranging from 10 to 250 microns.

2. A method for nasal adminstration according to claim 1, wherein said base is a water-abosrbing and water-insoluble substance selected from the group consisting of cellulose, starche, protein, cross-linked vinyl polymer and gum.

3. A method for nasal administration according to claim 1, wherein said base is a water-absorbing and water-insoluble cellulose.

4. A method for nasal adminstration according to claim 3, wherein said water-absorbing and water-insoluble cellulose is selected from the group consisting of crystalline cellulose, cellulose, α-cellulose, and cross-linked sodium carboxymethyl cellulose.

5. A method for nasal adminstration according to claim 3, wherein said water-absorbing and water-insoluble cellulose is crystalline cellulose.

6. A method for nasal adminstration according to claim 1, wherein said base is a water-abosrbing and water-insoluble cross-linked vinyl polymer.

7. A method for nasal administration according to claim 6, wherein said water-absorbing and water-insoluble cross-linked vinyl polymer is selected from the group consisting of cross-linked polyvinyl pryolidone and cross-linked carboxy vinyl polymer.

8. A method for nasal adminstration according to claim 1, wherein said water-absorbing and water-insoluble base is jointly used with a water-abosrbing and water-soluble base, wherein said water-absorbing and water-soluble base is employed in an amount of 0.1 to 60 wt % based on the weight of said water-absorbing and water-insoluble base.

9. A method for nasal administration according to claim 8, wherein said water-absorbing and water-soluble base is selected from the group consisting of a lower alkyl ether of cellulose, polyacrylate, polyethylene glycol and polyvinyl pyrolidone.

10. A method for nasal administration according to claim 1, wherein the physiologically active polypeptide or its derivative is a polypeptide or its derivative with a molecular weight of 1,000 to 300,000.

11. A method for nasal administration according to claim 1, wherein the physiologically active polypeptide or its derivative is a water-soluble polypeptide or its derivative.

12. A method for nasal administration according to claim 1, wherein the physiologically active polypeptide or its derivative is a peptide hormone.

13. A method for nasal adminstration according to claim 12, wherein the peptide hormone is selected from the group consisting of calcitonin, insulin, luteinizing hormone releasing hormone, desmopressin, vasopressin and oxytocin.

14. A method for nasal administration according to claim 1, wherein the physiologically active polypeptide or its derivative is a vaccine.

15. A method for nasal administration according to claim 14, wherein the vaccine is influenza vaccine or pertussis vaccine.

16. A method for nasal administation according to claim 1, wherein the physiologically active polypeptide or its derivative is a physiologically active protein.

17. A method for nasal administration according to claim 16, wherein the physiologically active protein is interferon.

18. A method for nasal adminstration according to claim 1, wherein said water-absorbing and water-insoluble base is employed in an amount of more than 10 times the weight of said polypeptide or its derivative.

* * * * *